(12) United States Patent
MacDonald et al.

(10) Patent No.: US 9,839,344 B2
(45) Date of Patent: Dec. 12, 2017

(54) CANNULA ASSEMBLY

(71) Applicant: Arthroptics, L.L.C., Washington Township, MI (US)

(72) Inventors: Jordan MacDonald, Washington Township, MI (US); Christian Calyore, Naples, FL (US); Yi-Ting Lee, Ann Arbor, MI (US); Nandini Ravi, Evanston, IL (US); Adrienne Alimasa, Madison, WI (US)

(73) Assignee: Arthroptics, L.L.C., Washington Township, MI (US)

( * ) Notice: Subject to any disclaimer, the term of this patent is extended or adjusted under 35 U.S.C. 154(b) by 350 days.

(21) Appl. No.: 14/656,778

(22) Filed: Mar. 13, 2015

(65) Prior Publication Data

US 2015/0272617 A1    Oct. 1, 2015

Related U.S. Application Data

(60) Provisional application No. 61/954,232, filed on Mar. 17, 2014.

(51) Int. Cl.
| | |
|---|---|
| *A61B 17/34* | (2006.01) |
| *A61B 1/05* | (2006.01) |
| *A61B 1/00* | (2006.01) |
| *A61B 90/00* | (2016.01) |

(52) U.S. Cl.
CPC ...... *A61B 1/00183* (2013.01); *A61B 1/00135* (2013.01); *A61B 1/05* (2013.01); *A61B 17/3417* (2013.01); *A61B 17/3421* (2013.01); *A61B 17/3474* (2013.01); *A61B 90/361* (2016.02); *A61B 2017/349* (2013.01); *A61B 2017/3445* (2013.01); *A61B 2017/3454* (2013.01); *A61B 2017/3458* (2013.01); *A61B 2217/005* (2013.01); *A61B 2217/007* (2013.01)

(58) Field of Classification Search
CPC ............ A61B 17/3415; A61B 17/3417; A61B 17/3474; A61B 17/3421; A61B 1/05; A61B 1/00183; A61B 1/00135; A61B 90/361; A61B 2017/3445; A61B 2017/3458
See application file for complete search history.

(56) References Cited

U.S. PATENT DOCUMENTS

| | | | | |
|---|---|---|---|---|
| 2006/0235458 | A1* | 10/2006 | Belson | A61M 25/0032 606/191 |
| 2008/0294123 | A1* | 11/2008 | Lunn | A61B 17/3462 604/256 |

* cited by examiner

*Primary Examiner* — Timothy J Neal
(74) *Attorney, Agent, or Firm* — Warn Partners, P.C.

(57) ABSTRACT

A cannula assembly including a camera system to help provide multiple viewing angles of a surgical site. This added visualization provides the surgeon with more comprehensive feedback during the surgical procedure, leading to better patient outcome and a reduction in the surgical failure rate. The cannula has a main lumen and a smaller secondary lumen and is insertable into the surgical site for easy surgeon adaptation. The camera is coupled to the secondary lumen toward the side of the cannula. This allows the camera to provide visualization without obstructing the main lumen for the use of tools. The camera wiring runs through a long tube connected to the camera and through a handle at the end of the tube without blocking access to the surgical site.

21 Claims, 6 Drawing Sheets

CANNULA ASSEMBLY

CROSS-REFERENCE TO RELATED APPLICATION

The instant application claims priority to U.S. Provisional Patent Application Ser. No. 61/954,232 filed Mar. 17, 2014. The disclosure of the above application is incorporated herein by reference.

FIELD OF THE INVENTION

The present invention relates to a cannula system with at least a pair of lumen and an imaging device used for surgical procedures.

BACKGROUND OF THE INVENTION

Arthroscopic surgery is increasingly being preferred over open surgery due to its minimally invasive nature and shorter post-surgery recovery time. Current estimates state that there are 4 million arthroscopic procedures each year in the United States. During each procedure, surgeons typically use 2 to 3 cannulas: one is occupied by the arthroscope and the others are utilized for the insertion of surgical tools. The arthroscope provides only a single, two-dimensional vantage point of the joint during surgery. If the surgeon wants to view the surgical site from a different angle, the arthroscope must be moved from one cannula to another. Pressure fluctuations may occur, resulting in turbulent saline flow within the joint and increased bleeding that can hinder visualization. In addition, the single field of view provided by the arthroscope is limited, which may result in imprecision, and consequently lower the surgical success rate. In addition, current technology does not allow for instrumentation and visualization from the same portal, such that the ideal view afforded by the arthroscope may often need to be compromised to permit instrumentation of the pathology. These visualization setbacks, along with a lack of standardization in the current surgical technique, can lead to a surgical failure rate that exceeds 40% in certain joints. The ability to view and use an instrument from the same portal may afford several advantages, including less incisions and soft tissue trauma, improved visualization, and consequently, surgical accuracy. Furthermore, the ability to visualize without active handling of the arthroscope may eliminate the need for trained surgical assistants and improve surgical efficiency.

BRIEF SUMMARY OF THE INVENTION

The present invention is a cannula-camera system to help provide multiple viewing angles of the surgical site. This added visualization will provide the surgeon with more comprehensive feedback during the surgical procedure, leading to better patient outcome and a reduction in the surgical failure rate. The cannula has a lumen portion comprising main lumen and a smaller secondary lumen. A modified trocar is inserted into the lumen portion. The cannula is then inserted into the surgical site in a similar way to current cannulas for easy surgeon adaptation. Once inside the body cavity the trocar is removed for insertion of an imaging device and surgical tools. The imaging device is housed in a long tube and is inserted through the designed secondary lumen on one side of the cannula. This allows the imaging device to provide visualization without obstructing the main lumen for the use of tools. The imaging device wiring runs through the housing and out of the handle without blocking access to the site. In another embodiment the imaging device is inserted through the lumen portion, rotated to outside the cannula, and pulled back through a slit in the cannula. A plurality of cannulas are usable simultaneously within the joint to provide tool interaction and additionally video output with multiple views to a monitor.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE SEVERAL VIEWS OF THE DRAWING

The present invention will become more fully understood from the detailed description and the accompanying drawings, wherein.

DETAILED DESCRIPTION OF THE INVENTION

The following description of the preferred embodiment(s) is merely exemplary in nature and is in no way intended to limit the invention, its application, or uses.

Referring to FIGS. 1-11 generally, in accordance with the present invention, there is provided a cannula assembly generally shown at 10 for surgical procedures such as performed within joint areas of the body or other areas.

The cannula assembly 10 includes a cannula generally indicated at 12 that is threaded and a cap portion generally indicated at 14. A trocar generally shown at 18 (FIG. 9) is selectively inserted into the cannula assembly 10 for inserting the assembly 10 into a body cavity, as will be explained in further detail below. The threads 16 on the external surface of the cannula 12 generally assist with holding placement in the body cavity.

The cannula assembly 10 includes a lumen portion with at least two adjoining lumen comprising a main lumen 20 and at least one secondary lumen 22. Either of the lumen 20, 22 are generally tubular shaped with smooth walls for easy passage of surgical tools and/or an imaging device. Generally, the lumen 20, 22 have the same diameter. Typically, the diameter of the secondary lumen 22 is smaller than the diameter of the main lumen 20. Preferably, the main lumen 20 is at least about double the diameter of the secondary lumen 22. Most preferably, the diameter of the main lumen 20 is at least about 1.0 inches and the secondary lumen 22 is less than 0.5 inches. The secondary lumen 22 has an opening 60 along its length to the main lumen 20.

The cannula 12 includes a bifurcation indicated generally at 24 comprising a first port 26 and a second branch 28. The first port 26 is in fluid communication with at least the main lumen 20 for fluid release to clear contaminated saline or other substances from the body joint space. A threaded valve cap 30 is removable from the end of the first port 26 for providing a connection point with any tubing or other secondary conduit for suction of the saline from the joint space. The second branch 28 has a tapped hole on the opposite side for insertion of a set screw 32 that allows a user to lock the translation and rotation of a long tube 34 by turning a second cap 36.

The cannula assembly 10 also includes a larger diameter portion generally shown at 38 integrally formed with the cannula 12, the larger diameter portion 38 comprising a first chamber 40 that generally funnels to the end of the main lumen 20 and is open to either lumen 20, 22 of the cannula 12. The larger diameter portion 38 is provided with a seal 42, most preferably, a two-layer silicone seal. A smaller diameter portion 44 (FIG. 8) of the cap portion 14 is inserted into the open end of the larger diameter portion 38 of the assembly to secure the seal 42 in place. The seal 42 prevents the outflow of pressurized saline from within the joint. A plurality of tabs 46 are provided on the cap portion 14 to attach the cap to the larger diameter portion 38, such as by snap fit engagement with each of a plurality of opposing first apertures of the larger diameter portion 38. Alternatively, the tabs 46 are disposed on the larger diameter portion 38 and the smaller diameter portion 44 has apertures.

Referring to FIGS. 1-2, 5 and 7 generally, in accordance with a first embodiment of the present invention, an imaging assembly or visualization tool or assembly generally indicated at 48 includes the long tube 34 that is attached to a handle 50 at one end and coupled to an imaging device 52 such as a camera device at a second end. The long tube 34 is operably sized for inserting into the secondary lumen 22 and housing wiring 56 for the imaging device 52. The wiring 56 passes through the handle 50 which has at least one second aperture 54 for the wiring 56 to exit out of the handle 50 without blocking access to the surgical site. Wireless communications with video feeds are contemplated.

The cannula assembly 10 is provided with a locking mechanism to lock the imaging assembly in place to prevent rotation. The locking mechanism can be the set screw 32. Alternatively, or in addition to the set screw 32, the outside of the secondary lumen 22 of the cannula 12 is provided with a slit 58 having a predetermined length to provide a locking mechanism. The slit 58 does not extend the entire length of the cannula 12 and is operably sized to receive and retain a portion of the imaging device 52. The imaging assembly 48 with the imaging device 52 is aligned with the end of the cannula with the imaging device 52 aligned to the main lumen 20 and the tube 34 aligned to the secondary lumen 22. The imaging assembly 48 is inserted through the entire cannula 12 and is then rotated, e.g., 180 degrees, until the imaging device 52 is outside the cannula 12, and is then retracted back along the side of the distal end of the cannula 12 through the slit 58.

The cap portion 14 is provided with a segmented portion indicated generally at 62 that acts as a first guide for the handle 50 to allow 180 degree rotation of the handle 50, the guide comprising at least two raised segments 64 that act as stops to prevent further degrees of rotation. Thus, the segment portion 62 interacts with the imaging assembly 48 to act as a guide and allow for a distinct predetermined amount of rotation of the imaging assembly 48, providing a key like mechanism or interaction where the segment portion 62 acts as the guide and the handle of the imaging assembly 48 acts as a key.

Figure 1:
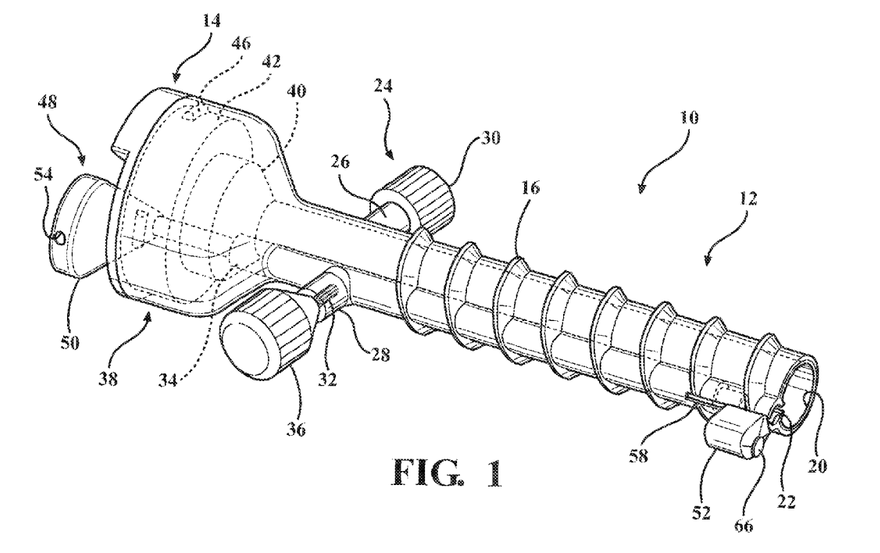
FIG. 1 is a perspective view of a cannula assembly with some portions in phantom and having an exterior imaging device, in accordance with one embodiment of the present invention.
Figure 1A:
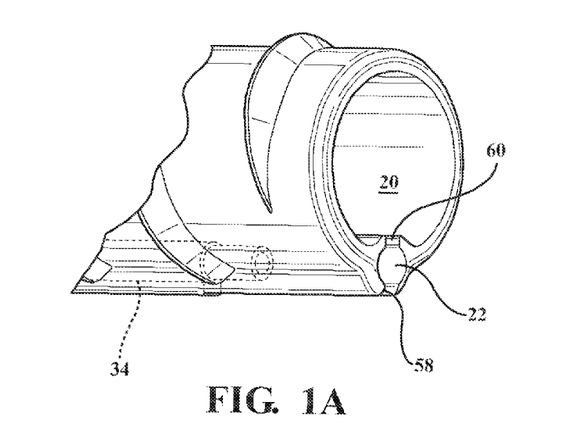
FIG. 1A is an enlarged view of the distal end of the cannula assembly of FIG. 1 depicting a slit and with the imaging device omitted for clarity, in accordance with the present invention.
Figure 2:
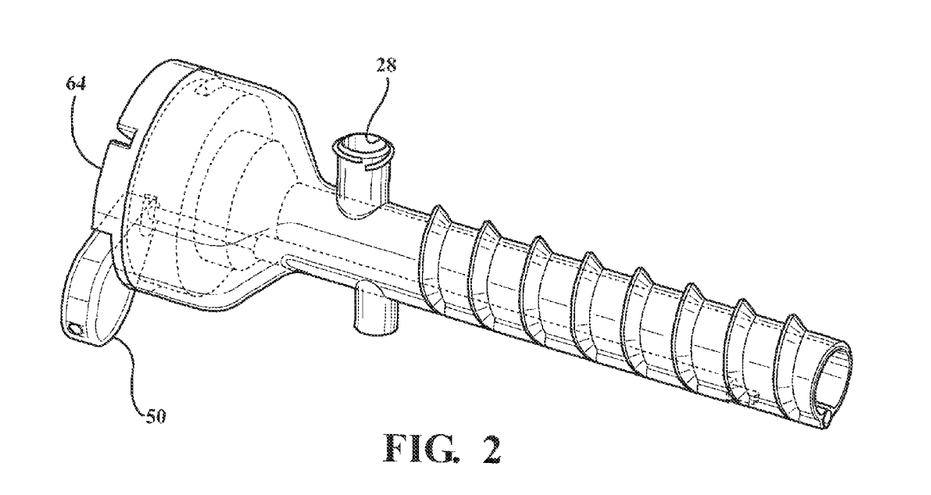
FIG. 2 is a perspective view of the cannula assembly of FIGS. 1-2 with the imaging device omitted for clarity, in accordance with the present invention.

The imaging device 52 is provided with a lens 66 and lighting source. The lens 66 is flat, and, alternatively, angled. By way of non-limiting example, angled to look at different angles of about 30 degrees either direction instead of straight on.

Figure 3:
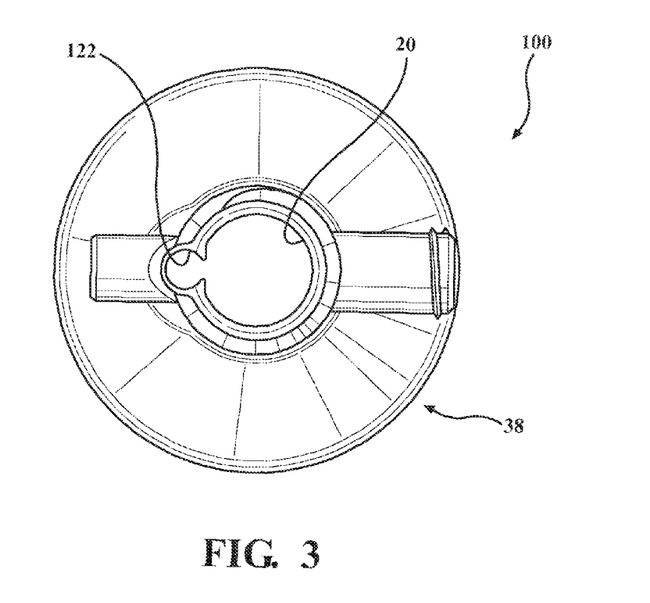
FIG. 3 is a bottom plan view of a cannula assembly, in accordance with a second embodiment of the present invention.
Figure 4:
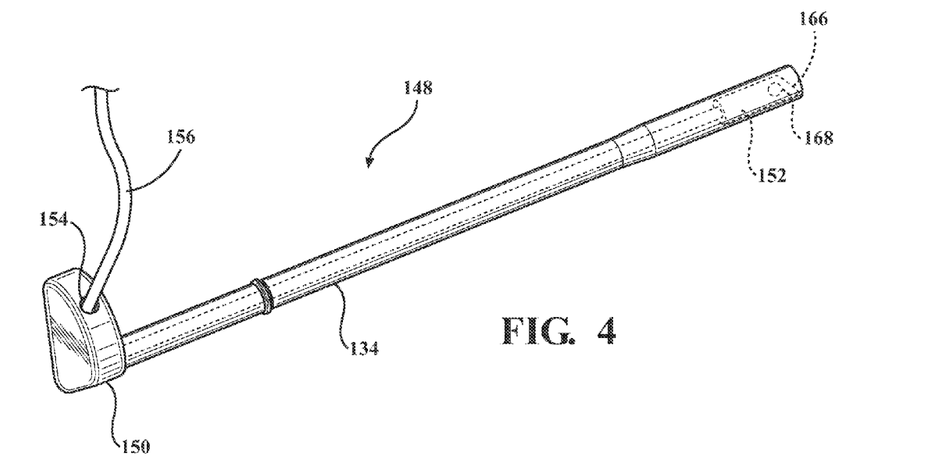
FIG. 4 is a perspective view of an imaging assembly of the cannula assembly having an internal imaging device, in accordance with the second embodiment of the present invention.

Referring to FIGS. 3-4 generally, in accordance with a second embodiment of the present invention, the cannula assembly 100 is identical to the first embodiment except that there is no outside slit in the secondary lumen 122 of the cannula 12 and the imaging assembly has an internal imaging device or camera; not an externally located imaging device. The imaging assembly or visualization tool or assembly generally indicated at 148 includes the long tube 134 that is attached to the handle 150 at one end. Toward the other end and located within the long tube 134 is an imaging device 152. The long tube 134 is operably sized for aligning with and sliding into the secondary lumen 122 and for housing wiring 156 for the imaging device 152 within the tube. The handle 150 has at least one second aperture 154 for wiring 156 of the imaging device 152 to exit out of the handle 150 without blocking access to the surgical site. Wireless communications/video feeds are contemplated.

As with the first embodiment, a locking mechanism is provided. Most preferably, the locking mechanism is the set screw 32. No segmented portion 62 with raised segments 64 is required. Alternatively, the cap portion 14 is provided with the segmented portion 62 that acts as a guide for the handle 150 to allow controlled rotation of the handle 150, and thereby of the imaging device 152 disposed therein.

The imaging device 152 is provided with a lens 166 and lighting source 168. The lens 166 is angled a predetermined amount to look at different angles. Most preferably, angles of about 30 degrees in either direction instead of straight on or any other angle suitable for particular surgical application. Alternatively, the lens 166 is flat.

Figure 5:
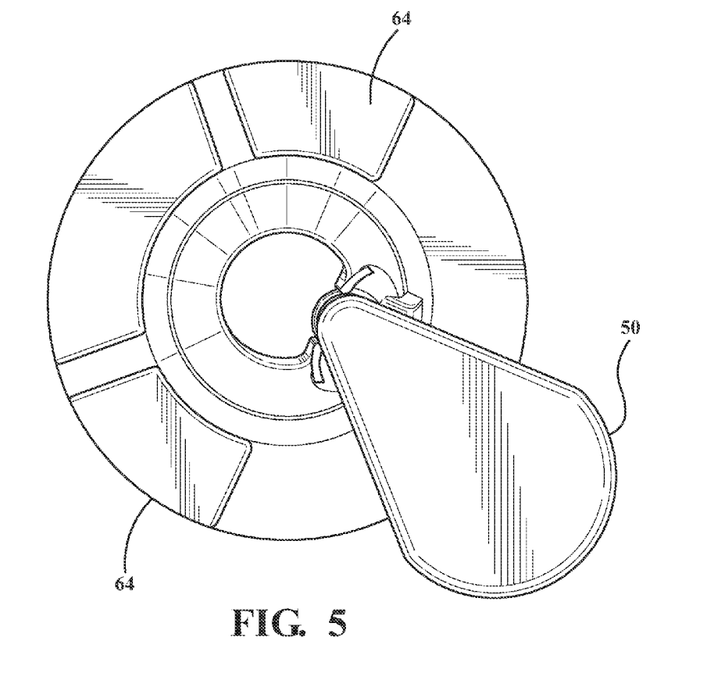
FIG. 5 is a top plan view of the cannula assembly, in accordance with either embodiment of the present invention.
Figure 6:
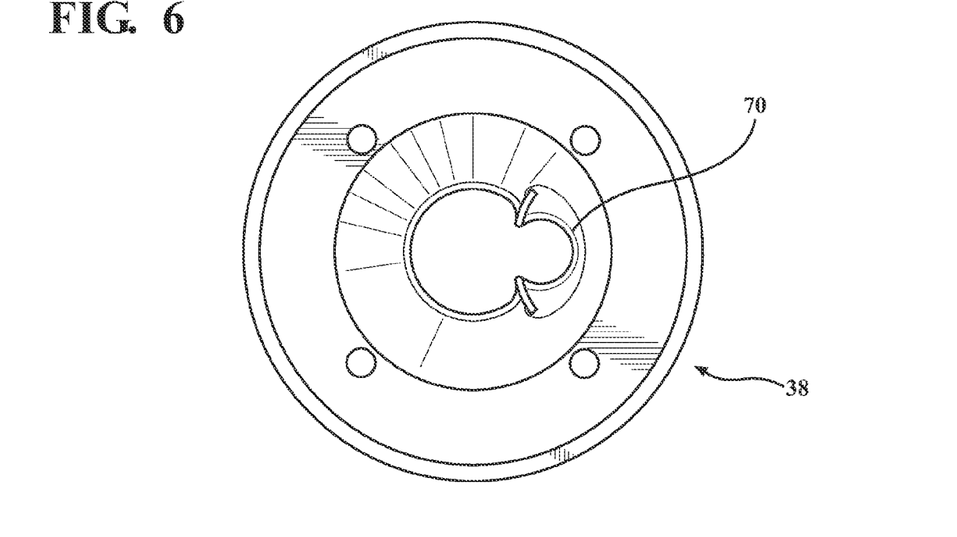
FIG. 6 is a top plan view of a cannula of the cannula assembly, in accordance with either embodiment of the present invention.
Figure 7:
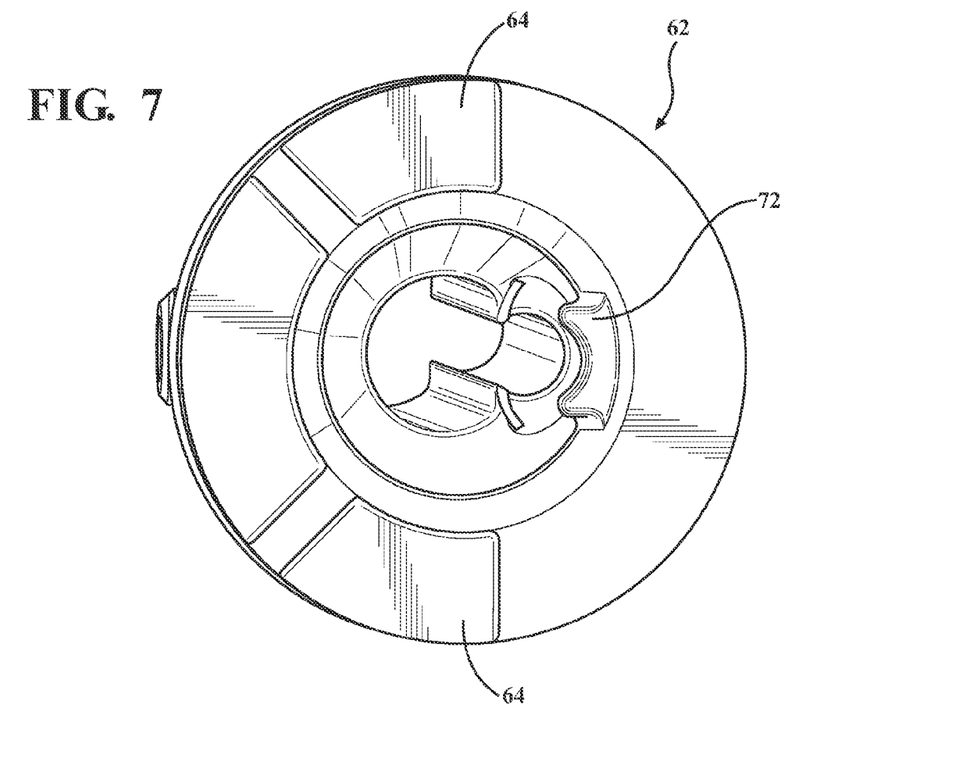
FIG. 7 is a top perspective view of the cannula assembly with a handle omitted for clarity, in accordance with either embodiment of the present invention.
Figure 8:
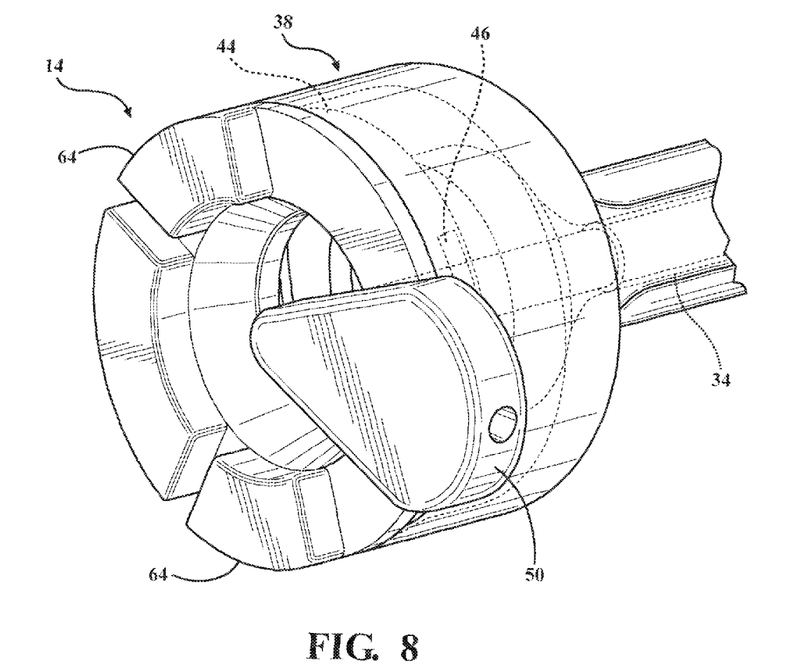
FIG. 8 is a perspective view of the cannula assembly, in accordance with the present invention.

Referring to FIGS. 5-7 generally, in either embodiment in accordance with the present invention, the larger diameter portion 38 of the cannula assembly includes a second guide 70 adjacent the secondary lumen 22 to guide the tube 34, 134 of the imaging assembly 48, 148. The cap portion 14 is provided with a third guide 72 adjacent to the second guide 70 to guide the tube 34, 134.

Figure 9:
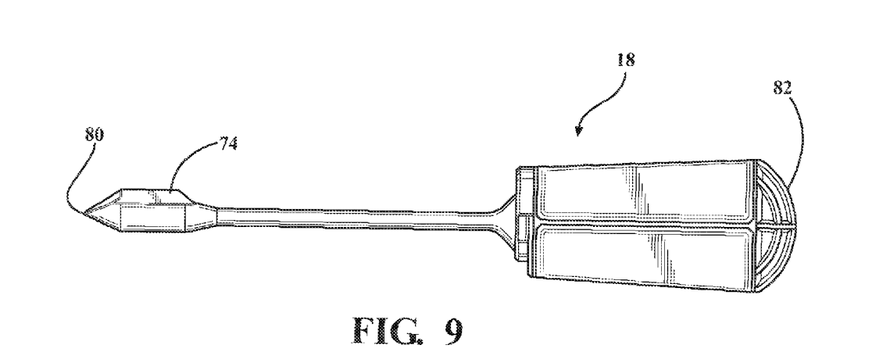
FIG. 9 is a side elevation view of a trocar of the cannula assembly used with either embodiment of the present invention.
Figure 10:
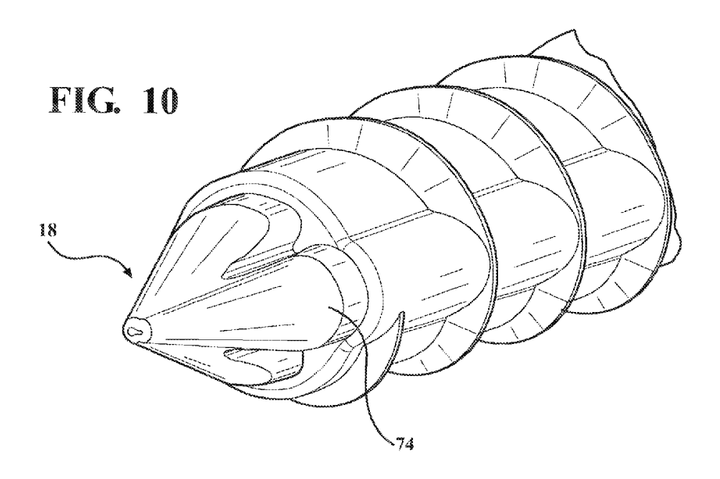
FIG. 10 is a perspective view of the distal end of the cannula assembly with a trocar, in accordance with the present invention.

Referring to FIGS. 9-10 generally, in either embodiment in accordance with the present invention, the trocar 18 is inserted into the cannula 12 for inserting the cannula assembly 10 into the body cavity. The trocar 18 freely slides within the lumen portion of the cannula assembly 10. When inserted, the trocar 18 fills the distal ends of both the main and secondary lumen 20, 22 so that nothing from inserting into the body cavity enters either of the lumen 20, 22. The trocar 18 is provided with a second projection 74 that fills the secondary lumen 22 of the cannula 12, which prevents tissue build up during insertion into the joint. The trocar 18 has a sharper tip 80 on the distal end, that when inserted into the cannula, is outside the distal end of the cannula 12. The trocar 18 also has a handle 82 on the proximal end of the trocar 18 for grasping by a user.

Figure 11:
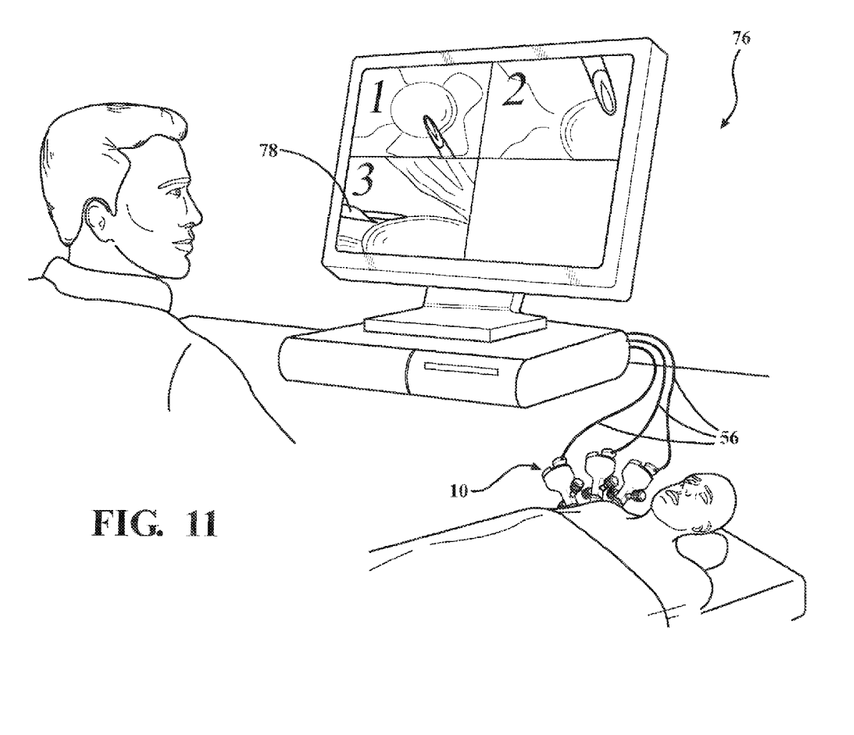
FIG. 11 is a schematic illustrating three cannula assemblies within a body cavity for a joint and video feeds to a monitor device.

Referring to FIG. 11 generally, in either embodiment in accordance with the present invention, once the cannula is within the body cavity, the trocar 18 is removed by the user and tools and/or the imaging assembly 48, 148 are selectively inserted into the cannula 12. Wiring 56, 156 from the imaging device 52, 152 exits the aperture 54, 154 of the handle 50, 150 and is connected to a multiplexer for video feed to a monitor indicated generally at 76. A plurality of cannula assemblies 10 are insertable into the joint area, e.g., at least three cannulas 10, for multiple views and access points to the site for using tools. FIG. 11 illustrates three quadrants shown on the screen with different vantage points provided by each cannula inserted in the shoulder joint. Each surgical tool, e.g., suturing devices 78, extending through the main lumen 20 into the body cavity are shown in a respective quadrant fed from each of the imaging devices 52, 152 of the respective cannula assembly 10. Thus, each suturing device is extending from the main lumen 20 while each imaging device 52, 152 is either within the secondary lumen 22 or on the outside of the secondary lumen 22, providing an unobstructed view to the site and suturing device for the user to view on the monitor. The multiplexer has many different options for viewing the distinct feeds, such as picture-in-picture, split screen, full screen and much more.

Preferably, the cannula assembly 10 is disposable. Generally, the cannula 12 is made of a rigid or semi-rigid material. Typically, at least the cannula 12 is made of a medical-grade resin. Preferably, at least the cannula 12 is made of a rigid medical-grade resin with clarity or that is transparent. Most preferably, a medical-grade resin substantially simulating the properties and aesthetics of polycarbonate is used.

Parts, with the exception of the threaded portion of the set screw 32, were prototyped with Accura60 resin using a Viper si2™ SLA® machine. The imaging device 52 and/or 152, by way of non-limiting example, is an Omnivision OV6922 image sensor. 28 AWG enamel coated wires are used to connect the imaging device to a 3V power source and the multiple inputs are transmitted to a multiplexer for a simultaneous video feed.

The description of the invention is merely exemplary in nature and, thus, variations that do not depart from the essence of the invention are intended to be within the scope of the invention. Such variations are not to be regarded as a departure from the spirit and scope of the invention.

What is claimed is:

1. A disposable cannula assembly, comprising:
    a cannula with a proximal and distal end with a lumen portion that is comprised of a main lumen and at least one secondary lumen that is an additional non-concentric tube of the same or smaller diameter than the main lumen and that extends from the proximal to distal end, the at least one secondary lumen connected with the main lumen by an opening that extends the entire length of the secondary lumen;
    a cap portion to secure a seal in place;
    a trocar that, toward a distal end of the trocar, has a complimentary shape that fills the distal end of the main lumen and the secondary lumen of the cannula, the trocar having a tip on the distal end and a handle on a proximal end of the trocar, the trocar freely slides within the main lumen and secondary lumen of the cannula; and
    an imaging assembly with a proximal end comprising a handle and a distal end comprising an imaging device, the imaging device being selectively inserted into the secondary lumen when the trocar is removed.

2. The disposable cannula assembly of claim 1, further comprising a bifurcation located near the proximal end of the cannula, wherein the bifurcation comprises a first port with a removable valve cap to allow for easy connection to flow or suction tubing.

3. The disposable cannula assembly of claim 2, wherein the bifurcation further comprises a second branch that has a tapped hole for insertion of a rotatable set screw forming a locking mechanism to selectively contact and lock the imaging assembly in place to prevent translation and rotation of the imaging assembly.

4. The disposable cannula assembly of claim 1, wherein the trocar fully fills the space of the distal end of the cannula lumen portion to prevent tissue build up during insertion of the cannula assembly into a body cavity, said trocar being easily insertable and removable from the cannula.

5. The disposable cannula assembly of claim 1, wherein the imaging assembly further comprises a long tube connected to the handle at one end, and the imaging device is connected toward the distal end of the long tube.

6. The disposable cannula assembly of claim 5, wherein the secondary lumen is substantially tubular and sized to allow the passage of the tube of the imaging assembly.

7. The disposable cannula assembly of claim 5, further comprising a second guide located adjacent the secondary lumen to align and guide the tube of the imaging assembly into the secondary lumen.

8. The disposable cannula assembly of claim 5, wherein the imaging assembly further comprises at least one wire for the imaging device, the at least one wire runs within the tube and out of at least one aperture formed within the handle.

9. The disposable cannula assembly of claim 8, wherein the imaging device is connectable to an image processor by the at least one wire and coupled to a display.

10. The disposable cannula assembly of claim 9, wherein the image processor is a multiplexer and the display feeds from multiple imaging devices of a plurality of cannula assemblies simultaneously in real time.

11. The disposable cannula assembly of claim 5, wherein the imaging device is located inside the long tube toward the distal end of the long tube.

12. The disposable cannula assembly of claim 5, wherein the distal end of the imaging device or tube has an angled lens for different angled views or a straight lens.

13. The disposable cannula assembly of claim 1, wherein the cap portion further comprising at least two exterior raised segments to act as stops for the handle to limit rotation of the handle of the imaging assembly to not exceed 180 degrees.

14. The disposable cannula assembly of claim 13, further comprising a third guide incorporated with the cap portion, the third guide operable to align and guide a tube of the imaging assembly into the secondary lumen.

15. The disposable cannula assembly of claim 1, further comprising a slit incorporated on the outside of the cannula for receiving a portion of the imaging assembly, said slit does not extend the entire length of the cannula.

16. The disposable cannula assembly of claim 15, wherein the slit is formed in the wall of the secondary lumen and the imaging device is connected on the exterior of a long tube of the imaging assembly, such that after said imaging device is inserted through the entire lumen portion using the long tube and handle of the imaging assembly, the imaging assembly is rotated 180 degrees by the handle, and the imaging device is then retracted back along the side of the distal end of the cannula through the slit.

17. The disposable cannula assembly of claim 1, wherein the imaging device further comprises at least one light source incorporated to adequately illuminate the surgery space.

18. The disposable cannula assembly of claim 1, wherein the imaging assembly when inserted into the cannula does not block the main lumen and allows the passage of surgical instruments in the main lumen.

19. The disposable cannula assembly of claim 1, wherein the tip is sharp.

20. A disposable cannula assembly, comprising:
a cannula with a proximal and distal end with a lumen portion that is comprised of a main lumen and at least one secondary lumen that is an additional non-concentric tube of smaller diameter than the main lumen and that extends from the proximal to distal end, the at least one secondary lumen connected with the main lumen by an opening that extends the entire length of the secondary lumen;
a cap portion to secure a seal in place to prevent the outflow of pressurized fluid;
a trocar that has a complimentary shape, including a second projection, located toward a distal end of the trocar that fills the distal end of the main lumen and the secondary lumen of the cannula, wherein the second protrusion fills the shape of the distal end of the secondary lumen, the trocar having a tip on the distal end and a handle on a proximal end of the trocar, the trocar freely slides within the lumen portion of the cannula and is selectively removable; and
an imaging assembly with a proximal end comprising a handle connected to a tube and a distal end comprising an imaging device connected to the tube, the imaging device being selectively inserted into the secondary lumen when the trocar is removed;
wherein the imaging assembly when inserted into the cannula does not block the main lumen and allows the passage of surgical instruments in the main lumen.

21. A disposable cannula assembly, comprising:
a cannula comprising a main lumen and at least one secondary lumen that is an additional non-concentric tube of the same or smaller diameter than the main lumen, the at least one secondary lumen having an opening to the main lumen that extends the entire length of the secondary lumen;
a cap portion attached to a larger diameter portion of the cannula to secure a seal in place located within the larger diameter portion to prevent the outflow of pressurized fluid from the surgery space;
a trocar that, toward a distal end of the trocar, has a complimentary shape that fills the distal end of the main lumen and the secondary lumen of the cannula, the trocar having a tip on the distal end and a handle on a proximal end of the trocar, the trocar freely slides within the main lumen and secondary lumen of the cannula and is selectively removable; and
an imaging assembly with a proximal end comprising a handle connected to a tube and a distal end comprising an imaging device connected to the tube, the imaging assembly being selectively inserted into the secondary lumen when the trocar is removed, said imaging device located within the tube or outside the cannula;
wherein the imaging assembly when inserted into the cannula does not block the main lumen and allows the passage of surgical instruments in the main lumen.

* * * * *